United States Patent [19]

Svec et al.

[11] Patent Number: 5,527,788
[45] Date of Patent: Jun. 18, 1996

[54] METHOD AND COMPOSITION FOR TREATING OBESITY COMPRISING DEHYDROEPIANDROSTERONE (DHEA), OR A DERIVATIVE THEREOF, AND AN ANORECTIC AGENT

[75] Inventors: Frank Svec; Johnny Porter, both of Metairie, La.

[73] Assignee: Louisiana State Univ. Medical Center Foundation, New Orleans, La.

[21] Appl. No.: 184,191

[22] Filed: Jan. 18, 1994

[51] Int. Cl.⁶ .................. A61K 31/56; A61K 31/495; A61K 31/415; A61K 31/135
[52] U.S. Cl. .................. 514/169; 514/178; 514/181; 514/231.5; 514/402; 514/651; 514/653; 514/879; 514/909
[58] Field of Search ................ 514/169, 178, 514/181, 231.5, 402, 879, 909, 653, 651

[56] References Cited

U.S. PATENT DOCUMENTS

| | | | |
|---|---|---|---|
| 2,408,345 | 9/1946 | Shelton et al. | 564/381 |
| 3,001,910 | 9/1961 | Schutte | 514/255 |
| 3,198,833 | 8/1965 | Beregi et al. | 564/381 |
| 3,520,975 | 7/1970 | Alphin et al. | 514/291 |
| 3,622,675 | 11/1971 | Koppe et al. | 514/522 |
| 3,930,009 | 12/1975 | Timms | 514/393 |
| 3,968,245 | 7/1976 | Higuchi | 514/653 |
| 4,255,439 | 3/1981 | Cooper | 514/392 |
| 4,416,894 | 11/1983 | Woodhouse | 514/292 |
| 4,452,815 | 6/1984 | Wurtman et al. | 514/654 |
| 4,518,595 | 5/1985 | Coleman et al. | 514/178 |
| 4,557,934 | 12/1985 | Cooper | 514/159 |
| 4,594,358 | 6/1986 | Hynes | 514/651 |
| 4,626,549 | 12/1986 | Molloy et al. | 514/651 |
| 4,666,898 | 5/1987 | Coleman et al. | 514/177 |
| 4,839,382 | 6/1989 | Maestrone et al. | 514/453 |
| 4,871,726 | 10/1989 | Applezweig et al. | 514/177 |
| 4,895,845 | 1/1990 | Seed | 514/252 |
| 4,897,390 | 1/1990 | Ruhe | 514/177 |
| 4,898,694 | 2/1990 | Schwartz et al. | 540/94 |
| 4,940,585 | 7/1990 | Hapworth et al. | 424/464 |
| 4,956,388 | 9/1990 | Robertson et al. | 514/651 |
| 4,978,532 | 12/1990 | El-Rashidy | 424/448 |
| 5,001,119 | 3/1991 | Schwartz et al. | 514/177 |
| 5,006,517 | 4/1991 | Bradlow et al. | 514/178 |
| 5,019,594 | 5/1991 | Wurtman et al. | 514/561 |
| 5,096,712 | 3/1992 | Wurtman | 424/422 |
| 5,157,031 | 10/1992 | Schwartz et al. | 514/177 |

OTHER PUBLICATIONS

Bray, "The Zucker-Fatty Rat: A Review," *Federation Proceedings*, 36, pp. 148–153 (1977).
Cleary, "The Antiobesity Effect Of Dehydroepiandrosterone In Rats," *Proc. Soc. Exp. Biol. Med.*, 196, pp. 8–16 (1991).
Darga et al., "Fluoxetine's Effect On Weight Loss In Obese Subjects," *The American Journal of Clinical Nutrition*, 54, pp. 321–325 (1991).
Gray et al., "A Randomized Double-Blind Clinical Trial Of Fluoxetine In Obese Diabetics," *International Journal of Obesity*, 16, pp. S67–S72 (1992).
McGuirk et al., "Effects Of Chronically Administered Fluoxetine and Fenfluramine On Food Intake, Body Weight And The Behavioural Satiety Sequence," *Psychopharmacology*, 106, pp. 401–407 (1992).
Pomerleau et al., "Effects Of Fluoxetine On Weight Gain and Food Intake In Smokers Who Reduce Nicotine Intake," *Psychoneuroendocrinology*, 16, pp. 433–440 (1991).
Visser et al., "The Effect Of Fluoxetine On Body Weight, Body Composition and Visceral Fat Accumulation," *International Journal of Obesity*, 17, pp. 247–253 (1993).
White et al., "Responsiveness Of Isolated Adrenocortical Cells From Lean And Obese Zucker Rats to ACTH," *Am. J. Physiol.*, 225, pp. E229–E235 (1988).
Wright et al., "Divergent Effect Of Dehydroepiandrosterone On Energy Intakes Of Zucker Rats," *Physiology & Behavior*, 53, pp. 39–43 (1993).
Garattini et al., "From Fenfluramine Racemate To d-Fenfluramine," *Annals Of The New York Academy Of Sciences*, 499, Human Obesity, Wurtman et al., eds., pp. 156–166 (1987).
Physicians' Desk Reference, 47th Edition, pp. 710–711, 857–858, 943–946, 1053, 1403–1404, 1949–1950, 2126–2127, 2305–2306 (Medical Economics Data, NJ, (1993).
Abadie et al., "Effect Of Dehydroepiandrosterone On Neurotransmitter Levels And Appetite Regulation Of The Obese Zucker Rat," *Diabetes*, 42, pp. 662–669 (1993).
Browne et al., "Dehydroepiandrosterone: Antiglucocorticoid Action In Mice," *Am. J. Med. Sci.*, 303, pp. 366–371 (1992).
Wright et al., "Antiglucocorticoid Action Of Dehydroepiandrosterone In Young Obese Zucker Rats," *Int. J. Of Obesity*, 16, pp. 579–583 (1992).
Van der Kar et al., "Serotonergic Neurons And Neuroendocrine Function," *NIPS*, 8, pp. 202–207 (1993).
Abadie et al., "Effects Of Dehydroepiandrosterone And/Or Fenfluramine On Macronutrient Selection And Hypothalamic Neurotransmitter Content In Zucker Rats," *Fed Am Soc Exp Biol. J.*, 7, A413 (1993).
Porter et al., "Fenfluramine FF Effects On Brain 5-Hydroxytryptamine 5-HT and 5-Hydroxyindoleacetic Acid 5-HIAA In the Obese Zucker Rat," *Fed Am Soc Exp Biol. J.*, 4, A376 (1990).
Porter et al., "Fenfluramine Effects On Food Intake Of The Obese Zucker Rats," *Fed Am Soc Exp Biol. J.*, 3, A353 (1989).
Hargrave et al., "Delta-4-Androstenedione And Feeding Inhibition In The Lean And Obese Zucker Rat," *Clinical Research*, 41, A756 (1993).

Primary Examiner—Marianne M. Cintins
Assistant Examiner—Kevin E. Weddington
Attorney, Agent, or Firm—Finnegan, Henderson, Farabow, Garrett & Dunner

[57] ABSTRACT

The invention describes a method and composition for treating obesity or related disorders in animals using an anorectic agent and dehydroepiandrosterone (DHEA). The composition effectively diminishes caloric intake, may alter metabolism, weight gain, or a combination thereof.

23 Claims, 10 Drawing Sheets

☐ CONTROL   ■ DHEA(D)   ▨ FENFLURAMINE(F)   ◨ DRUG D&F

☐ CONTROL   ■ DHEA (D)   ⊘ FENFLURAMINE (F)   ◊ DRUG D & F

☐ CPD. B 1 MG    ▨ CPD. B 5 MG    ■ DHEA 0.3 %
▨ DHEA +CPD. B 1 MG    ▨ DHEA +CPD. B 5 MG

METHOD AND COMPOSITION FOR TREATING OBESITY COMPRISING DEHYDROEPIANDROSTERONE (DHEA), OR A DERIVATIVE THEREOF, AND AN ANORECTIC AGENT

DESCRIPTION

A method and composition for treating obesity and related disorders in animals comprising dehydroepiandrosterone (DHEA), or a derivative thereof, and an anorectic agent.

FIELD OF THE INVENTION

This invention describes an effective method and composition for treating obesity and related disorders in humans and animals, such as dogs, cats, or any other suitable animal, using DHEA or a derivative thereof and an anorectic agent. The method and composition are useful in veterinary as well as human applications.

BACKGROUND OF THE INVENTION

Obesity may be the major health problem of the Western world. Nearly 20% of the United States' adult population is overweight and its prevalence is rising. The medical and economic importance of obesity go far beyond effects on self-image. Obesity is the dominant risk factor for the expression of adult-onset diabetes mellitus, and thus leads to complications of cardiovascular, renal, and peripheral vascular disease. Obesity is also a leading factor in the development of complications after surgical procedures.

Although obesity is probably a common endpoint for a variety of disorders, all causes of obesity have at least a period of hyperphagia in which the subject eats more food than needed for the current energy needs. Currently, there is no effective treatment for hyperphagia. The agents used, at best, work for only a few weeks or are clinically unsafe because of serious side effects.

This invention teaches the use of DHEA and one or more of the following anorectic agents for the treatment of obesity and related disorders in animals: fenfluramine hydrochloride (HCl), phentermine HCl, phendimetrazine tartrate, mazindol, diethylpropion HCl, and fluoxetine HCl. DHEA has been evaluated for its ability to modify food intake and/or weight when administered individually, but not in combination with the anorectic drugs disclosed in this invention. There was no appreciation in the art that the combined use of DHEA and one or more of the disclosed anorectic agents would have a significant and dramatic effect on the treatment of obesity and related disorders.

Dehydroepiandrosterone (DHEA) and its sulphated derivative, both major secretory products of the human adrenal, are naturally occurring steroids. Traditionally, DHEA has been called an adrenal androgen because it can be metabolized in the periphery to testosterone. DHEA itself cannot interact with the androgen receptor, and thus is not an androgen.

The effect of DHEA on food intake and obesity in the Zucker rat was studied by Cleary M. P., "The Antiobesity Effect of Dehydroepiandrosterone in Rats," *Proceedings of the Society for Experimental Biology and Medicine*, 196:8–16 (1991). This reference reports results showing administration of DHEA to rats caused a weight loss independent of food intake. Conflicting reports have been reported by others, who found that administration of DHEA decreased caloric intake in obese Zucker rats, but not in the lean animal. Wright et al., "Divergent Effect of Dehydroepiandrosterone on Energy Intakes of Zucker Rats," *Physiology & Behavior*, 53:39–43 (1993). The conflicting reports may reflect the different methods employed by the two groups in calculating food intake for the animals. Cleary measured daily cumulative food intake, in which changes are measured at the end of a period of time such as two weeks. Wright et al. measured daily intake and weight change for 7–8 days. An initial change was found within 24 hours. As the animals' weight and metabolism may have already changed with administration of the drug at the end of a two week period, the method of Wright et al. more clearly reflects the effect of the drug on the animal.

DHEA was also evaluated for its effect on obesity, serum lipids, and body fat in humans. Nestler et al., "Dehydroepiandrosterone Reduces Serum Low Density Lipoprotein Levels and Body Fat but Does not Alter Insulin Sensitivity in Normal Men," *J. Clin. Endocrinol. Metab.*, 66:57–61 (1988). Results showed DHEA in a divided dose of 1600 mg/person/day, corresponding to a dose of about 22 mg/kg/day, has no effect on either food intake or body weight in lean subjects, although it may have a slight effect on body fat content. Other researchers were unable to repeat the positive results. Welle et al., "Failure of Dehydroepiandrosterone to Influence Energy and Protein Metabolism in Humans," *Journal of Clinical Endocrintogy*, 71:1259–1264 (1990).

The anorectic drugs used in this invention include fenfluramine HCl, phentermine HCl, phendimetrazine tartrate, mazindol, diethylpropion HCl, and fluoxetine HCl. Tachyphylaxis and tolerance have been demonstrated with all drugs of this class used in the treatment of obesity. *Physician's Desk Reference.*, 47th edition, page 1053 (Medical Economics Data, Montvale, N.J., 1993), incorporated by reference. It has not been established that the action of such drugs in treating obesity is primarily one of appetite suppression, as other central nervous system actions or metabolic effects may be involved. *Physician's Desk Reference* at 1053. The drugs are not particularly effective, as the magnitude of increased weight loss of drug-treated patients over placebo-treated patients is only a fraction of a pound a week, with the rate of weight loss being greatest in the first weeks of therapy for both drug and placebo-treated subjects and decreasing in succeeding weeks as tolerance to the anorectic agent develops. *Physician's Desk Reference* at 1053.

Fenfluramine HCl, chemically known as N-ethyl-α-methyl-3(tri-fluoromethyl)benzeneethanamine hydrochloride, is an anorectic agent differing from prototype anorectic drugs used in the treatment of obesity in appearing to produce more central nervous system depression than stimulation. *Physician's Desk Reference* at 1949. Tolerance to the anorectic effect usually develops within a few weeks, requiring discontinuation of the use of the drug. *Physician's Desk Reference* at 1949. The drug is commercially available under the trade name PONDIMIN® Tablets (A. H. Robins Co.).

Phentermine hydrochloride, chemically known as phenyl-tertiary-butylamine hydrochloride, is a sympathomimetic amine with pharmacologic activity similar to the prototype drugs of this class used in obesity, the amphetamines. *Physician's Desk Reference* at 1053 and 2305. The drug is an anorectic compound with actions including central nervous system stimulation and elevation of blood pressure. *Physician's Desk Reference* at 1053. Tolerance to the anorectic effect usually develops within a few weeks, requiring discontinuation of the use of the drug. *Physician's Desk Reference* at 1053. The drug is commercially available under the trade names FASTIN® Capsules (SmithKline Beecham Pharmaceuticals) and ADIPEX-P® (Gate Pharmaceuticals).

Phendimetrazine tartrate, chemically known as (+)-3,4-dimethyl-2-phenylmorpholine tartrate, is another anorectic drug having an effect on appetite and the central nervous system. *Physician's Desk Reference* at 710, 857, and 2618. Tolerance to the anorectic effect usually develops within a few weeks, requiring discontinuation of the use of the drug. *Physician's Desk Reference* at 711. The drug is commercially available under the trade names PRELU-2® (Boehringer Ingelheim Pharmaceuticals, Inc.), BONTRIL® PDM and BONTRIL® SLOW-RELEASE (Carnrick Laboratories, Inc.), and PLEGINE® (Wyeth-Ayerst Laboratories).

Mazindol, chemically designated as 5-(4-chlorophenyl)-2,5-dihydro-3H-imidazo[2,1-$\alpha$]isoindol-5-ol, is an imidazoisoindole anorectic agent. *Physician's Desk Reference* at 2126. Although an isoindole, mazindol has pharmacologic activity similar to the prototype drugs used in obesity, the amphetamines. *Physician's Desk Reference* at 2126. Tolerance to the anorectic effect usually develops within a few weeks, requiring discontinuation of the use of the drug. *Physician's Desk Reference* at 2127. The drug is commercially available under the trade name SANOREX® (Sandoz Pharmaceuticals Corp.).

Diethylpropion hydrochloride, chemically known as 1-phenyl-2-diethylamino-1-propanone hydrochloride, is a sympathomimetic amine with actions including some central nervous system stimulation and elevation of blood pressure. *Physician's Desk Reference* at 1403. Tolerance to the anorectic effect usually develops within a few weeks, at which point the drug is discontinued. *Physician's Desk Reference* at 1403. Diethylpropion HCl is commercially available under the trade names TENUATE® and TENUATE DOSPAN® (Marion Merrell Dow Inc.).

Finally, fluoxetine HCl, chemically designated ($\pm$)-N-methyl-3-phenyl-3- [($\alpha,\alpha,\alpha$-trifluro-p-tolyl)oxy]propylamine hydrochloride, is a compound used as an antidepressant. *Physician's Desk Reference* at 943. The drug influences serotonergic transmission, a characteristic of anorectic agents. Van de Kar et al., "Serotonergic Neurons and Neuroendocrine Function," *NIPS*, 8:202–207 (1993). Significant weight loss can result with fluoxetine HCl treatment. *Physician's Desk Reference* at 944; Darga et al., "Fluoxetine's Effect on Weight Loss in Obese Subjects," *Am. J. Clin. Nutr.*, 54:321–5 (1991); and Visser et al., "The Effect of Fluoxetine on Body Weight, Body Composition and Visceral Fat Accumulation," *Int. J. Obes.*, 17:247–53 (1993). Fluoxetine HCl has not been systematically studied, in animals or humans, for its potential for tolerance. *Physician's Desk Reference* at 945–6. However, recent studies showed rapid development of tolerance with administration of fluoxetine and fenfluramine. McGuirk et al., "Effects of Chronically Administered Fluoxetine and Fenfluramine on Food Intake, Body Weight and the Behavioural Satiety Sequence," *Psychopharmocology* (Berl), 106:401–7 (1992). The drug is commercially available under the trade name PROZAC® (Dista Products Co.).

This invention fulfils a need in the art for an effective method for treating obesity and related disorders in animals. The method, employing a composition comprising DHEA or a derivative thereof and an anorectic agent, diminishes caloric intake, may affect metabolism, or a combination thereof, to produce a weight loss for the treated subject. Other objects and advantages of the invention are set forth in the following description. The accompanying drawings illustrate and, together with this description, explain the principle of the invention.

SUMMARY OF THE INVENTION

The present invention overcomes the problems and disadvantages associated with current strategies for treating obesity, such as the development of tolerance within a short period of time to the drugs currently employed, and provides a new therapy for the treatment of obesity and related disorders in animals. This invention describes the use of DHEA or a derivative thereof and at least one anorectic agent in combination to produce weight loss in animals.

A further embodiment of the invention is the additional administration of a glucocorticoid, along with the combination of DHEA or a derivative thereof and at least one anorectic agent, for the treatment of obesity and related disorders in animals.

BRIEF DESCRIPTION OF THE FIGURES

FIGS. 1 through 10 describe experimental results comprising administration of DHEA or an anorectic agent, such as fenfluramine HCl, phentermine HCl, mazindol, and diethylpropion HCl, or a combination of an anorectic agent and DHEA to lean and obese Zucker rats to determine the effect of the treatments on food intake and weight loss of the animals.

FIG. 1A shows the total caloric intake, FIG. 1B shows the total protein intake, FIG. 1C shows the total carbohydrate intake, and FIG. 1D shows the total fat intake, all measured at day 3.

FIG. 2A shows the total caloric intake, FIG. 2B shows the total protein intake, FIG. 2C shows the total carbohydrate intake, and FIG. 2D shows the total fat intake, all measured at day 3.

FIG. 6A shows the carbohydrate intake on day 3, FIG. 6B shows the change in body weight on day 4, and FIG. 6C shows the total caloric intake on day 3 of the test. P value shows the difference from the control.

FIG. 7A shows the daily fat consumption and FIG. 7B shows body weight gain over the trial. P value shows the difference from the control.

FIG. 8A shows the fat intake, FIG. 8B shows the carbohydrate intake, and FIG. 8C shows the body weight change over the time of the trial. P value shows the difference from the control.

FIG. 9: The effect of corticosterone and DHEA individually and in combination on the body weight of lean Zucker rats is shown. Six groups of animals were established: the first (control) group; a second group receiving an injection of 1 mg/kg/day corticosterone in sesame oil ("Cpd B 1"); a third group receiving an injection of 5 mg/kg/day corticosterone in sesame oil ("Cpd B 5"); a fourth group receiving a diet supplemented with 0.3% DHEA ("DHEA"); a fifth group receiving 1 mg/kg/day corticosterone in sesame oil and a diet supplemented with 0.3% DHEA ("Cpd B 1+DHEA"); and a sixth group receiving an injection of 5 mg/kg/day corticosterone in sesame oil and a diet supplemented with 0.3% DHEA ("Cpd B 5+DHEA").

DESCRIPTION OF PREFERRED EMBODIMENTS

Figure 1A:
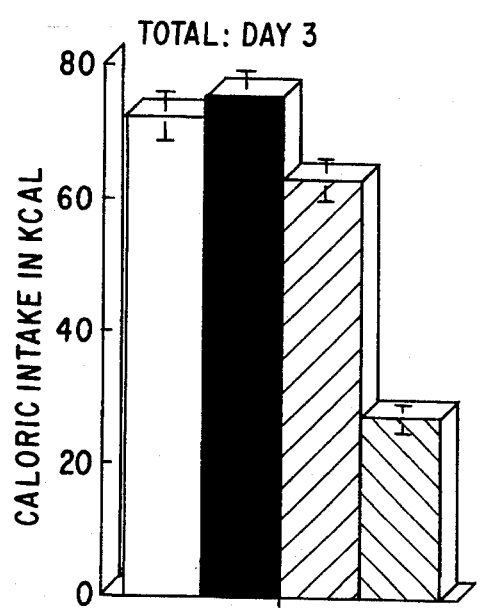
FIGS. 1A, 1B, 1C and 1D: The effect of fenfluramine and DHEA, given individually and in combination, on the caloric intake of carbohydrate, protein, and fat in lean Zucker rats is shown. Groups of lean rats were presented bowls of food containing nearly pure carbohydrate, protein, or fat. After an initial control period, the rats received fenfluramine (Drug F) at 5/mg/kg/day, DHEA (Drug D) at 100 mg/kg/day, or both fenfluramine and DHEA intraperitoneally daily for four days. A fourth group (control) received no drug. Caloric intake was measured and recorded each day, with the first day of drug treatment day 0 and the fourth day of treatment day 3. Values are the mean +SEM.

This invention describes dramatic diminishing of caloric intake and weight loss in animals with administration of a composition of DHEA or a derivative thereof and an anorectic agent. It was completely unexpected that the administration of DHEA or a derivative thereof and an anorectic agent would have such a synergistic effect on the treatment of obesity and related disorders. Furthermore, in sharp contrast to current methods of treating obesity and related disorders, with administration of an anorectic agent in combination with DHEA, tolerance to the composition over an extended period of time was not evident.

A further embodiment of the invention is the additional administration of a glucocorticoid, such as corticosterone, along with the combination of DHEA or a derivative thereof and the anorectic agent, for the treatment of obesity and related disorders in animals. The glucocorticoid is preferably administered in a dosage from about 1 mg/kg/day up to about 50 mg/kg/day, and more preferably in a dosage from about 5 mg/kg/day up to about 25 mg/kg/day.

The composition can be administered orally or parenterally, or a combination of oral and parenteral administration can be used. In addition, DHEA or a derivative thereof and the one or more anorectic agents can be administered as an addition to the food of the animal.

Derivatives of DHEA, such as 16-substituted androstanes and 16-substituted androstenes, are described in U.S. Pat. No. 5,001,119 to Schwartz et al., incorporated by reference. 17-hydroxy-steroids are described in U.S. Pat. No. 4,898,694 to Schwartz et al., incorporated by reference. α-HET and β-HET analogs are described in U.S. Pat. No. 4,897,390 to Ruhe, incorporated by reference. Such derivatives of DHEA, as well as metabolites of DHEA, such as Δ4-androstenedione, are useful in the claimed invention.

The anorectic agents that can be employed in the invention include fenfluramine hydrochloride (HCl), phentermine HCl, phendimetrazine tartrate, mazindol, diethylpropion HCl, and fluoxetine HCl.

In the present invention, the D–L racemate of fenfluramine was used in the experiments. The D–L and D isomers of fenfluramine differ in potency: the D isomer is a much more potent compound. Garattini et al., "From Fenfluramine Racemate to d-Fenfluramine," *Human Obesity*, Annals of the New York Academy of Sciences, vol. 499, Wurtman et al. eds., pages 156–166 (The New York Academy of Sciences, New York, N.Y., 1987). Thus, the difference between using the D isomer and the D–L racemate of fenfluramine is in the required dosage.

The composition of the invention can be administered either orally or parenternally. Preferable methods of administering the drugs are by injections, food supplements, transdermal patches, or rectal suppositories.

Pharmaceutically acceptable carriers for DHEA or a derivative thereof, the anorectic agent, or both, can also be employed. Such carriers can be sterile liquids, such as water, alcohol, dimethylsulphoxide (DMSO), oils, including petroleum oil, animal oil, vegetable oil, peanut oil, soybean oil, mineral oil, sesame oil, and the like. Also useful are carriers such as starch, sugar, lactose, magnesium stearate, stearic acid, cellulose, gelatin, talc, titanium dioxide, silica gel, tartaric acid, zinc stearate, povidone, glycerin, benzoic acid, iron oxide, silicone, and the like. Saline solutions, aqueous dextrose, and glycerol solutions can also be employed as liquid carriers, particularly for injectable solutions. Suitable pharmaceutical carriers are described in *Remington's Pharmaceutical Sciences,* 18th Edition (A. Gennaro, ed., Mack Pub., Easton, Pa., 1990), incorporated by reference.

The composition of the invention comprises at least one anorectic agent and DHEA in an amount effective in diminishing caloric intake, carbohydrate intake, fat intake, protein intake, or food intake, to produce a weight loss for the animal. In particular, the anorectic agent and DHEA are present in amounts which in combination are synergistically effective in treating obesity or a related disorder. Preferred dosages of DHEA or a derivative thereof and one or more anorectic agents are each from about 0.05 to about 200 mg/kg/day of each compound. In particular, the anorectic agent is administered in a dosage from about 0.05 mg/kg/day up to about 100 mg/kg/day, and DHEA is administered in a dosage from about 2.5 mg/kg/day up to about 100 mg/kg/day. More preferably, the anorectic agent is administered in a dosage from about 3 mg/kg/day up to about 25 mg/kg/day, and DHEA is administered in a dosage from about 25 mg/kg/day up to about 100 mg/kg/day. Most preferably, for a composition comprising DHEA and fenfluramine HCl, DHEA is present in an amount from about 25 mg/kg/day up to about 100 mg/kg/day, and dl-fenfluramine HCl is present in an amount from about 5 mg/kg/day up to about 10 mg/kg/day. If the d-isomer of fenflurmine is used, the fenflurmine is administered in a dosage of from about 2.5 mg/kg/day up to about 5 mg/kg/day.

This invention is applicable to treating any animal for obesity and related disorders. A further embodiment of the invention is the use of the disclosed compositions to produce lean animals, such as in livestock or veterinary applications.

The unexpected effect of the present invention is demonstrated in the following experiments and is depicted in FIGS. 1–10. In these experiments, the Zucker rat was used as an animal model for the invention because the animal is a good model of obesity, and because a colony of these animals was readily available. The obesity seen in the Zucker fatty rat shares many characteristics with some forms of human obesity; there is hyperphagia, hypoactivity, mild hyperglycemia, insulin resistance, and hypercorticosteronemia. White et al., "Responsiveness of Isolated Adrenocortical Cells From Lean and Obese Zucker Rats to ACTH," *Am J. Physol,* 255 (Endocrinol Metab 18):E229–E235 (1988); and Alarrayed et al., "Is There a Role for the Adrenals in the Development of Hypercholesterolemia in Zucker Fatty Rats," *Am J. physiol,* 263. (Endocrinol Metab 26):E287–E295 (1992). The animals have two phenotypes, obese and lean. The obese animal is characterized by hyperphagia, hyperinsulinism, and elevated lipids, with obesity beginning at age four weeks.

In many of the experiments the animals were fed a "macronutrient selection diet." In this paradigm, each animal is presented with three bowls of food. The food in the first bowl contains 90% of its calories as carbohydrate, the food in the second bowl contains 90% of its calories as protein, and the food in the third bowl contains 90% of its calories as fat. Animals are allowed to choose between the three bowls in the experiments. In general, both the obese and the lean animals selected a similar diet: 40–50% fat, 20% protein, and 30–40% carbohydrate. Interestingly, this is similar to the composition of the usual human diet.

Having generally described the invention, a more complete understanding can be obtained by reference to specific examples, which are provided herein for purposes of illustration only and are not intended to be limiting.

EXAMPLE 1

The effect of fenfluramine and DHEA, given both individually and in combination, on the caloric intake of carbohydrate, protein, and fat of lean Zucker rats was determined.

Female Zucker rats, aged 13–18 weeks, were obtained from the colony maintained in the Department of Physiology at Louisiana State University Dental School in New Orleans, La. All animals were maintained on a 12 hour light-dark cycle (lights on at 0600), with the temperature maintained at $22°\pm1°$ C.

Groups of lean rats were presented bowls of food containing nearly pure carbohydrate, protein, or fat. Each day consumption from each bowl was monitored, allowing a determination of total caloric, carbohydrate, protein, and fat intake. This enabled observing changes in an animals' choice of macronutrient.

Figure 1B:
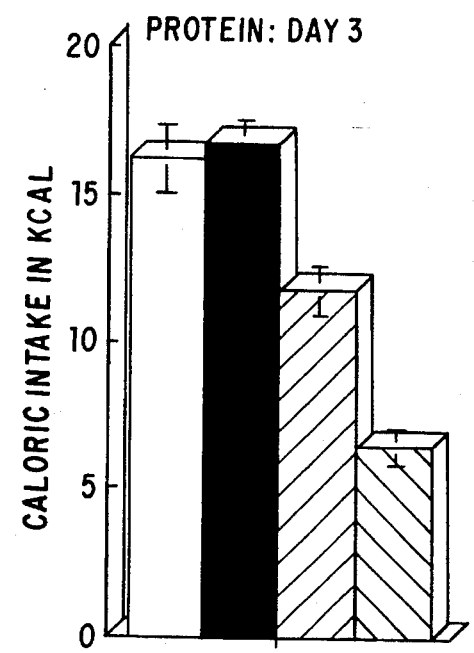
Figure 1C:
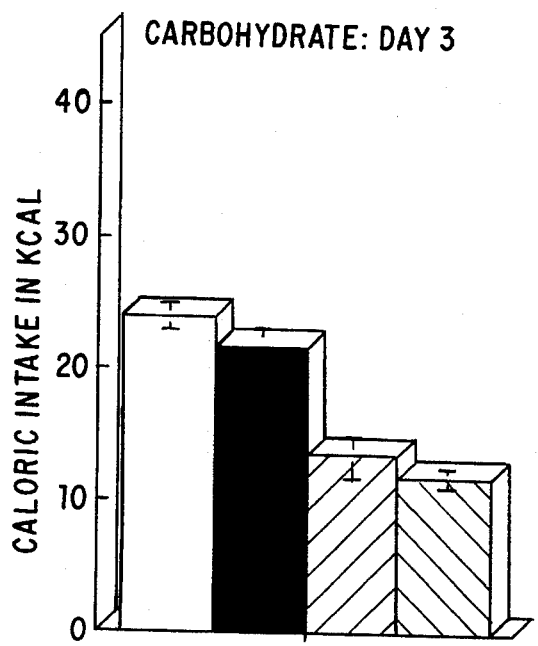
Figure 1D:
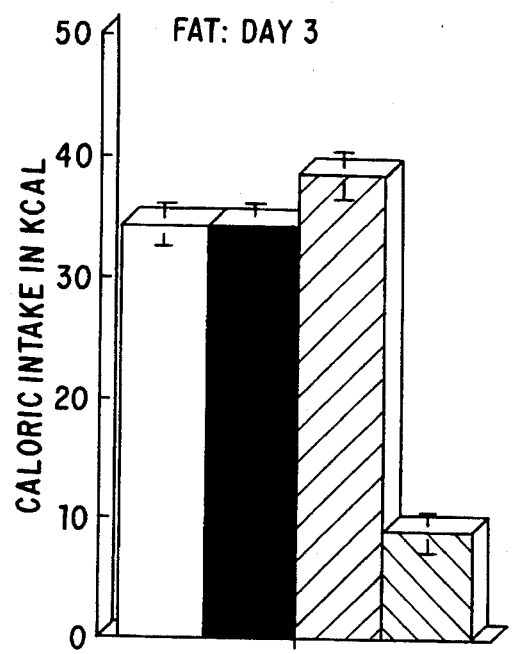
Figure 2A:
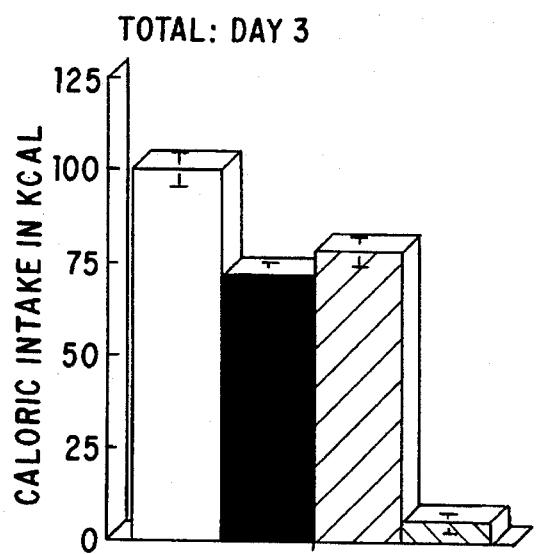
FIGS. 2A, 2B, 2C and 2D: The effect of fenfluramine and DHEA, given individually and in combination, on the caloric intake of carbohydrate, protein, and fat in obese Zucker rats is shown. Groups of obese rats were presented bowls of food containing nearly pure carbohydrate, protein, or fat. After an initial control period, the rats received fenfluramine (Drug F) at 5/mg/kg/day, DHEA (Drug D) at 100 mg/kg/day, or both fenfluramine and DHEA intraperitoneally daily for four days. A fourth group (control) received no drug. Caloric intake was measured and recorded each day, with the first day of drug treatment day 0 and the fourth day of treatment day 3. Values are the mean +SEM.
Figure 2B:
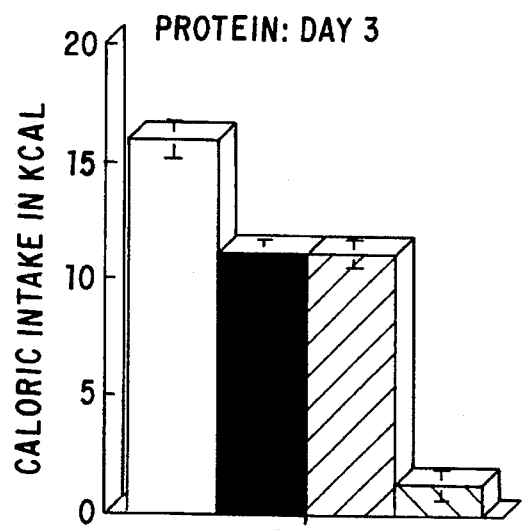
Figure 2C:
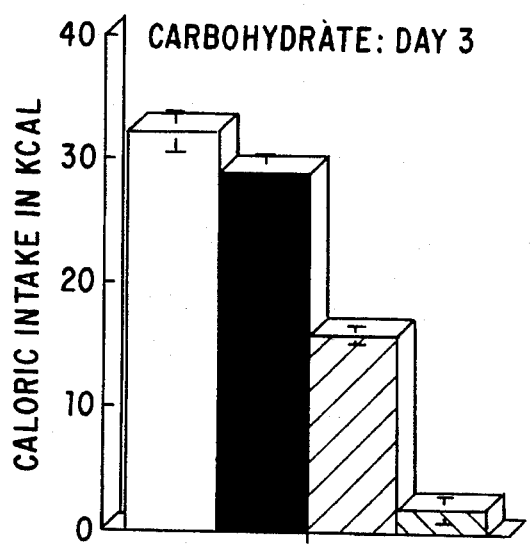
Figure 2D:
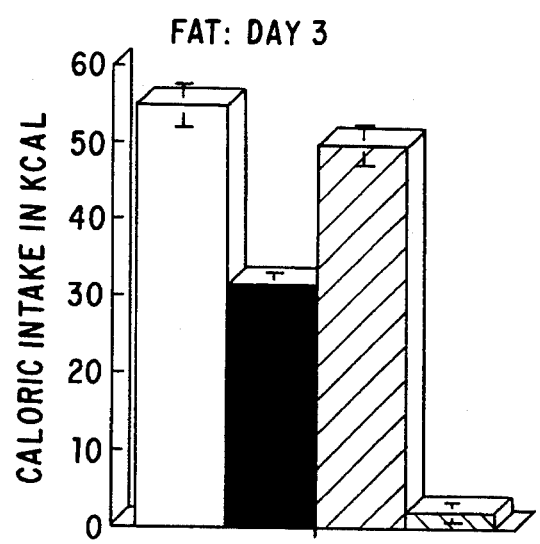
Figure 3A:
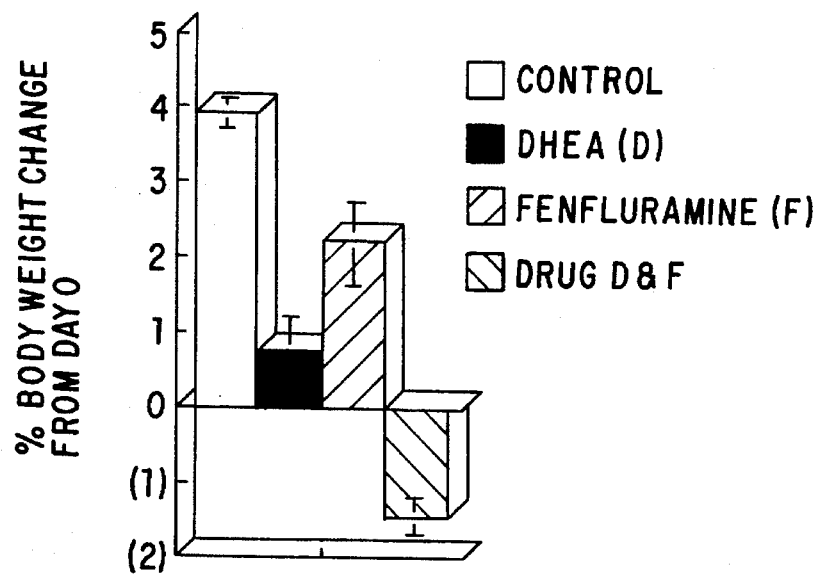
FIGS. 3A, 3B: The effect on the body weight of lean and obese Zucker rats with administration of fenfluramine and DHEA, given individually and in combination, is shown. The weight of the lean rats described in FIG. 1 is given in FIG. 3A and the weight of the obese rats described in FIG. 2 is given in FIG. 3B. For each group the increment of weight is expressed as a percentage of the initial body weight.
Figure 3B:
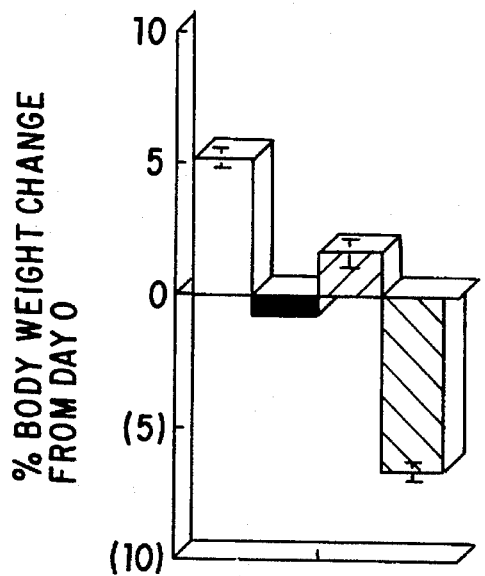

After an initial control period, the rats received fenfluramine at 5/mg/kg/day, DHEA at 100 mg/kg/day, or both fenfluramine and DHEA intraperitoneally. A fourth group (control) received no drug. Caloric intake was measured and recorded each day, with the first day of treatment day 0 and the fourth day of treatment day 3. Values are the mean +SEM. FIG. 1A shows the total caloric intake, FIG. 1B shows the total protein intake, FIG. 1C shows the total carbohydrate intake, and FIG. 1D shows the total fat intake, all measured at day 3.

The total intake of calories was not significantly affected by either DHEA or fenfluramine given individually. Fenfluramine given alone diminished carbohydrate intake. This was expected, as fenfluramine alters serotonin release and this affects carbohydrate preference.

The combination of fenfluramine and DHEA had a significant effect on both total intake of calories and carbohydrate intake. Total caloric intake fell by nearly two thirds. The effect is particularly dramatic in the consumption of fat, with the combination of fenfluramine and DHEA resulting in approximately 9 Kcal consumption of fat, as compared to approximately 34 Kcal consumption of fat in the control group. The animals were neither sick nor hyperactive. There was no obvious behavioral change that could account for this change.

EXAMPLE 2

This experiment is similar to example 1, except that obese, rather than lean, Zucker rats were used as the animal model.

The protocol was the same as in example 1. The results show an effect on intake with individual use of fenfluramine and DHEA. Fenfluramine causes a decrease in carbohydrate and protein intake, and DHEA reduces the intake of protein and fat for the obese animal. Most significantly, the combination of fenfluramine and DHEA is dramatically effective in curbing all food intake.

The obese rat is a model of youth-onset obesity, while the lean rat is a model of normal food-intake control mechanism. The results are most unexpected in the obese animal, as the obese animal's life is centered on eating; it usually spends its day sitting in its cage nibbling. Results showing a complete inhibition of food consumption for this animal are striking. Because this effect is also demonstrated in the lean animal, the results suggest the treatment has universal applicability for lean and obese subjects.

EXAMPLE 3

The effect on body weight of lean and obese Zucker rats with administration of fenfluramine and DHEA, given individually and in combination, is determined. The change in body weight of the lean rats described in FIG. 1 is given in FIG. 3A and the change in body weight of the obese rats described in FIG. 2 is given in FIG. 3B. For each group the increment of weight is expressed as a percentage of the initial body weight.

The control lean animals gained an additional 4% during the time of the experiment. Animals treated with fenfluramine or DHEA individually also gained weight, but at a slower rate. Surprisingly, the lean animals receiving fenfluramine and DHEA in combination actually lost weight.

Qualitatively, the results are the same with obese animals. The control animals gained weight and animals receiving DHEA or fenfluramine individually maintained their initial weight. Again, with administration of a combination of fenfluramine and DHEA, the animals showed a significant weight loss.

EXAMPLE 4

The problem with all currently available anorectic agents is the development of tolerance to the anorectic action within a short period of time. This experiment evaluates the long-term effects (28 days) of administration of fenfluramine and DHEA on lean Zucker rats, and whether tolerance develops to these drugs.

Four groups of four lean Zucker rats were established. One group received 5 mg/kg/day fenfluramine; a second group received rat chow supplemented with 0.6% DHEA; a third group received 5 mg/kg/day fenfluramine and rat chow supplemented with 0.6% DHEA; and a fourth group (control) received no medication. The weight of the food consumed on the indicated days is reported as calories in FIG. 4A and the weight of the animals on the corresponding days is recorded in FIG. 4B.

In this experiment rat chow was used as food. DHEA was administered as a dietary supplement rather than as a daily injection.

DHEA administered individually had no significant effect on the food intake of lean animals as the DHEA-treated animals consumed as much chow as the control animals. Fenfluramine administered individually caused an initial decrease in the consumption of the rat chow, but the effect waned by three weeks. The combined therapy of fenfluramine and DHEA again showed effectiveness in reducing food intake, even after 28 days.

Figure 4A:
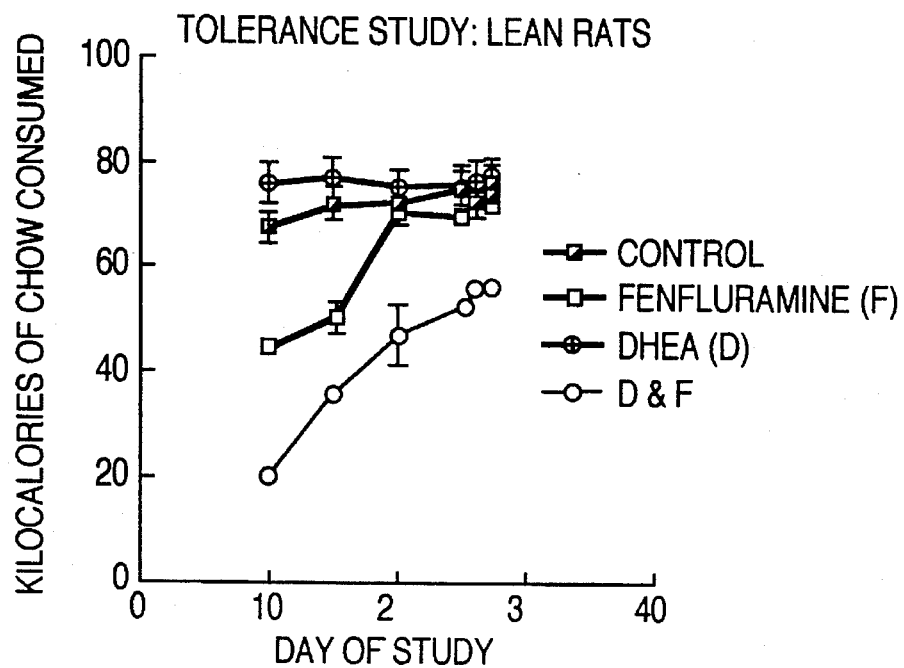
FIGS. 4A, 4B: The long-term effect of DHEA and fenfluramine, given individually and in combination, on the caloric intake and body weight of lean Zucker rats is shown. Four groups of four lean Zucker rats were established. One group received 5 mg/kg/day fenfluramine; a second group received rat chow supplemented with 0.6% DHEA; a third group received 5 mg/kg/day fenfluramine and rat chow supplemented with 0.6% DHEA; and a fourth group (control) received no medication. The weight of the food consumed on the indicated days is reported as calories in FIG. 4A and the weight of the animals on the corresponding days is recorded in FIG. 4B.
Figure 4B:
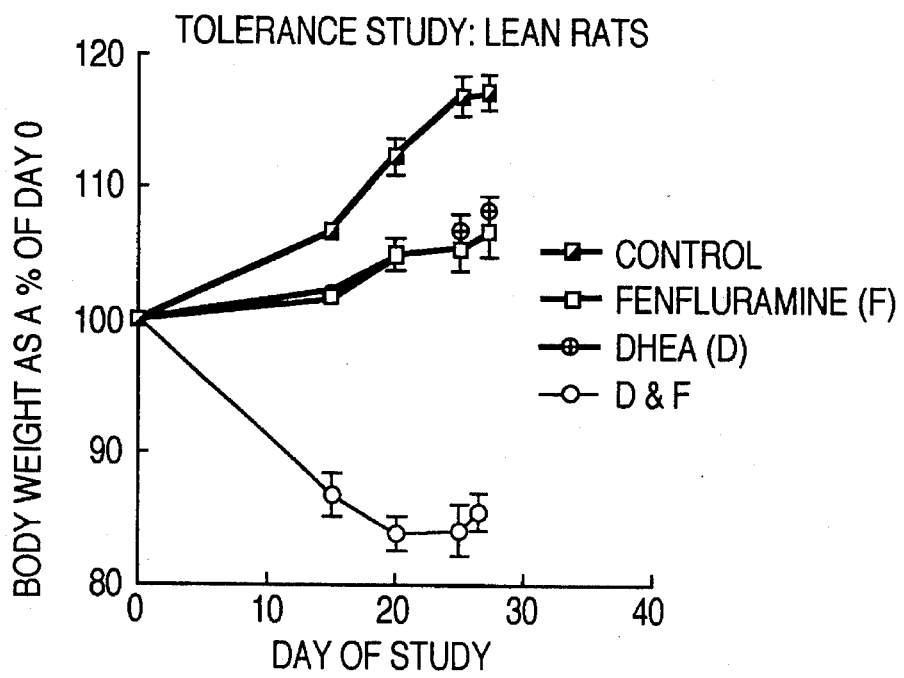
Figure 5A:
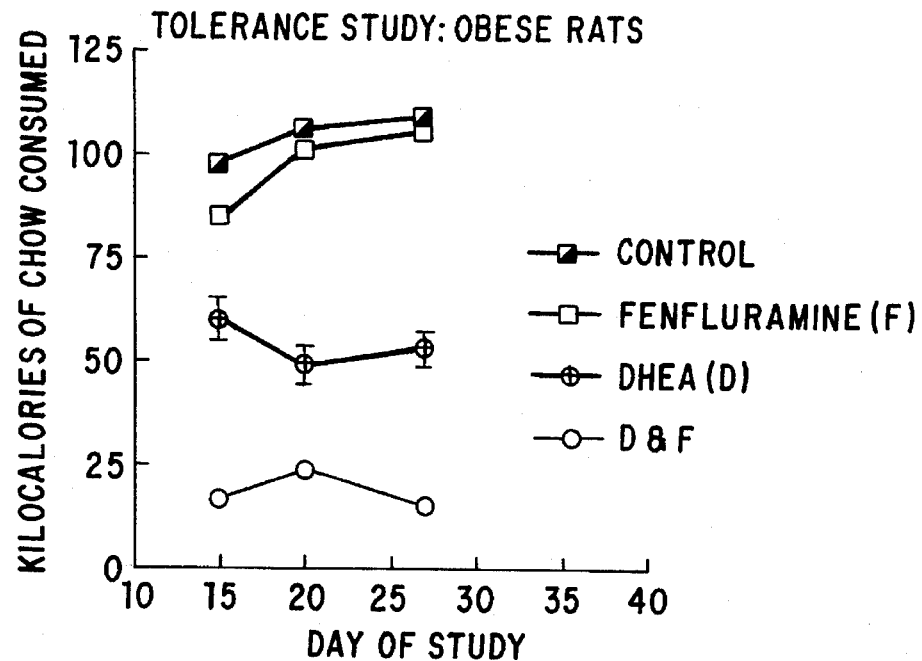
FIGS. 5A, 5B: The long-term effect of DHEA and fenfluramine, given individually and in combination, on the caloric intake and body weight of obese Zucker rats is shown. Four groups of four obese Zucker rats were established. One group received 5 mg/kg/day fenfluramine; a second group received rat chow supplemented with 0.6% DHEA; a third group received 5 mg/kg/day fenfluramine and rat chow supplemented with 0.6% DHEA; and a fourth group (control) received no medication. The weight of the food consumed on the indicated days is reported as calories in FIG. 5A and the weight of the animals on the corresponding days is recorded in FIG. 5B.
Figure 5B:
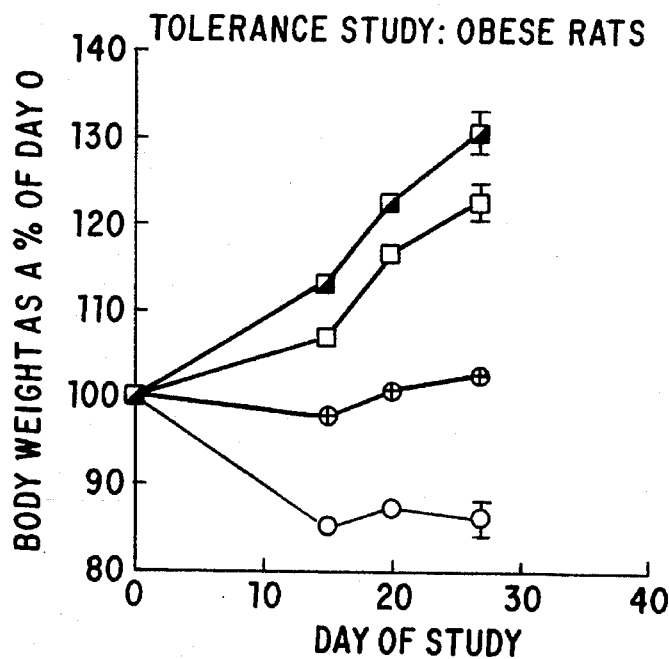

Changes in body weight of the treated animals corresponded to changes in caloric intake. FIG. 4B shows that animals treated with either fenfluramine or DHEA alone continued to gain weight. In contrast, animals receiving fenfluramine and DHEA in combination lost weight and stayed at this reduced weight.

EXAMPLE 5

This experiment is similar to example 4, except that obese, rather than lean, Zucker rats were used as the animal model. The protocol was the same as in example 4.

Fenfluramine administered individually produced a slightly significant depression in caloric intake on day 15. However, tolerance to the drug was evident by day 20 and 25. Administration of fenfluramine resulted in a small decrease in body weight in the obese animal. DHEA administered individually decreased food intake and stabilized the animals' weight gain.

In contrast to the poor results obtained with individual administration of the two drugs, favorable results showing a continued suppression of food intake and a weight loss were again obtained with the combined use of DHEA and fenfluramine.

EXAMPLE 6

The effect of mazindol and DHEA individually and in combination on the carbohydrate intake and body weight of lean Zucker rats was determined.

Figure 6A:
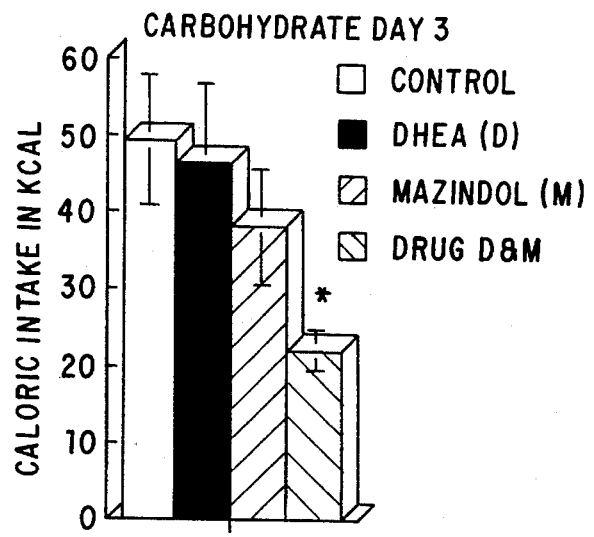
FIGS. 6A, 6B, 6C: The effect of mazindol and DHEA individually and in combination on the carbohydrate intake and body weight of lean Zucker rats is shown.
Figure 6B:
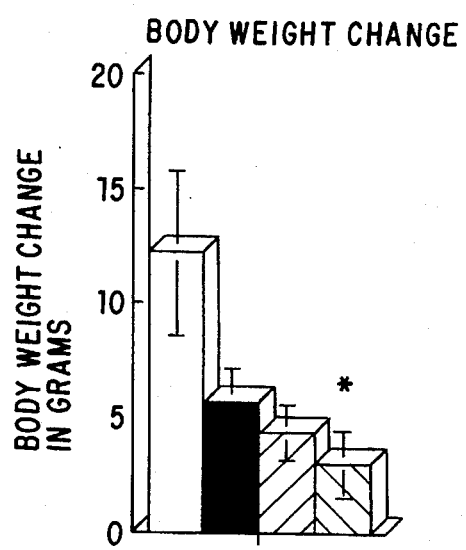
Figure 6C:
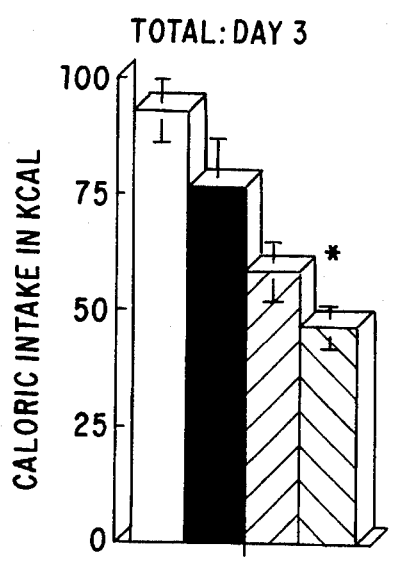

A first group of five animals was treated with 5 mg/kg/day mazindol, and a second group of five animals was treated with 5 mg/kg/day mazindol and 100 mg/kg/day DHEA for three days. A third group received 100 mg/kg/day DHEA for three days, and a fourth control group of five animals received only vehicle. FIG. 6A shows the carbohydrate intake on day 3, FIG. 6B shows the change in body weight on day 4, and FIG. 6C shows the total caloric intake on day 3 of the test.

The control group showed the largest carbohydrate intake, increase in body weight, and total caloric intake, followed by the group administered mazindol alone, and the group administered DHEA alone. The group receiving the combination of mazindol and DHEA evidenced the most significant decrease in carbohydrate intake, body weight, and total caloric intake.

EXAMPLE 7

The effect of phentermine HCl and DHEA individually and in combination on fat intake and body weight of lean Zucker rats was determined.

Figure 7A:
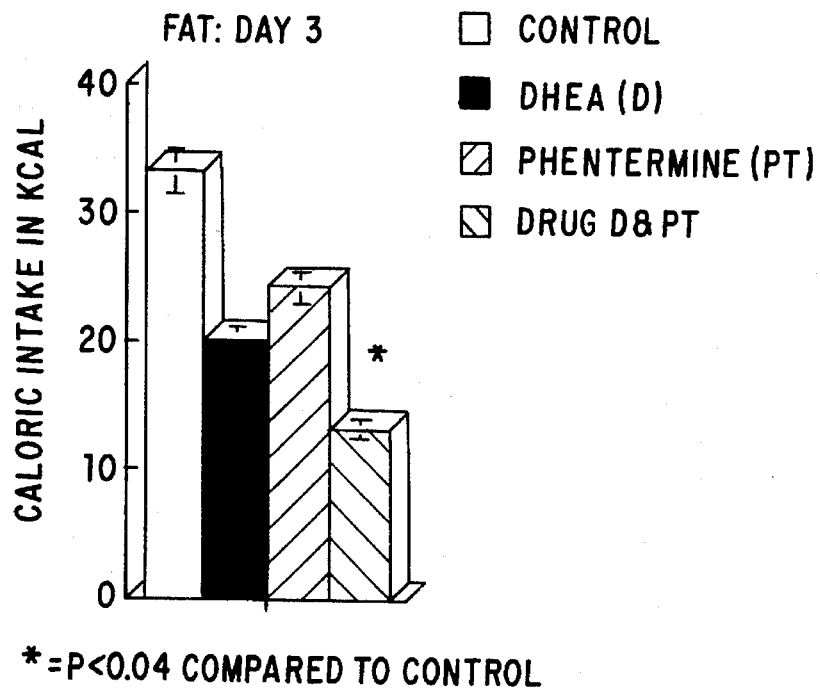
FIGS. 7A 7B: The effect of phentermine HCl and DHEA individually and in combination on fat intake and body weight of lean Zucker rats is shown.
Figure 7B:
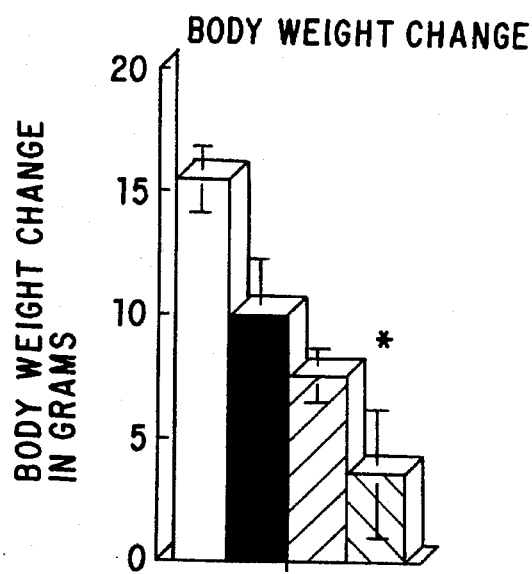
Figure 8A:
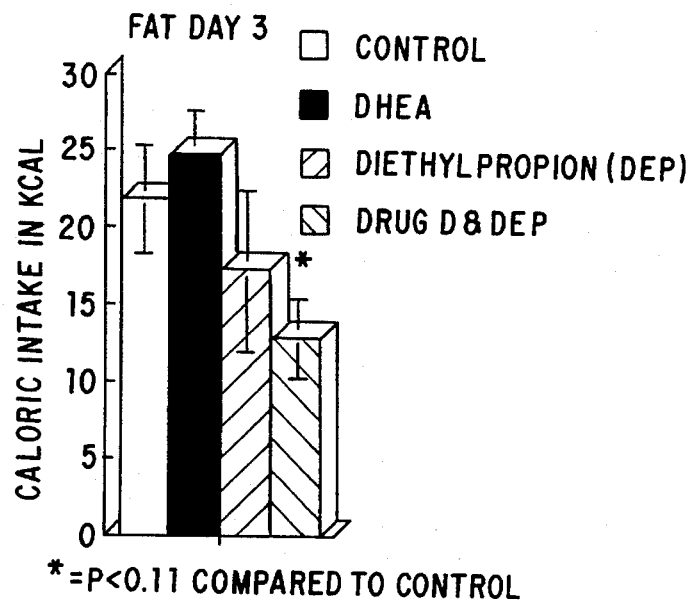
FIGS. 8A, 8B, 8C: The effect of diethylpropion HCl and DHEA individually and in combination on fat intake, carbohydrate intake, and body weight of lean Zucker rats is shown.
Figure 8B:
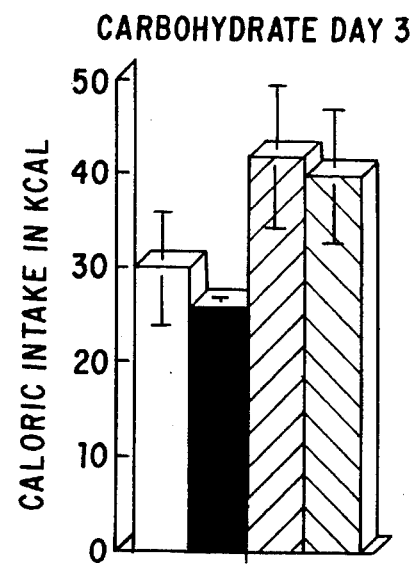
Figure 8C:
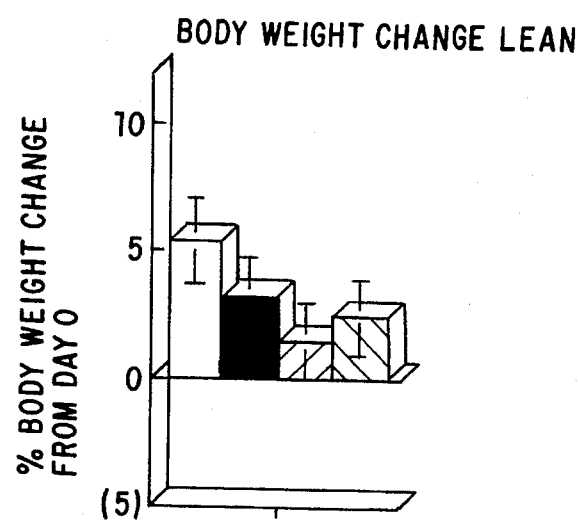
Figure 9:
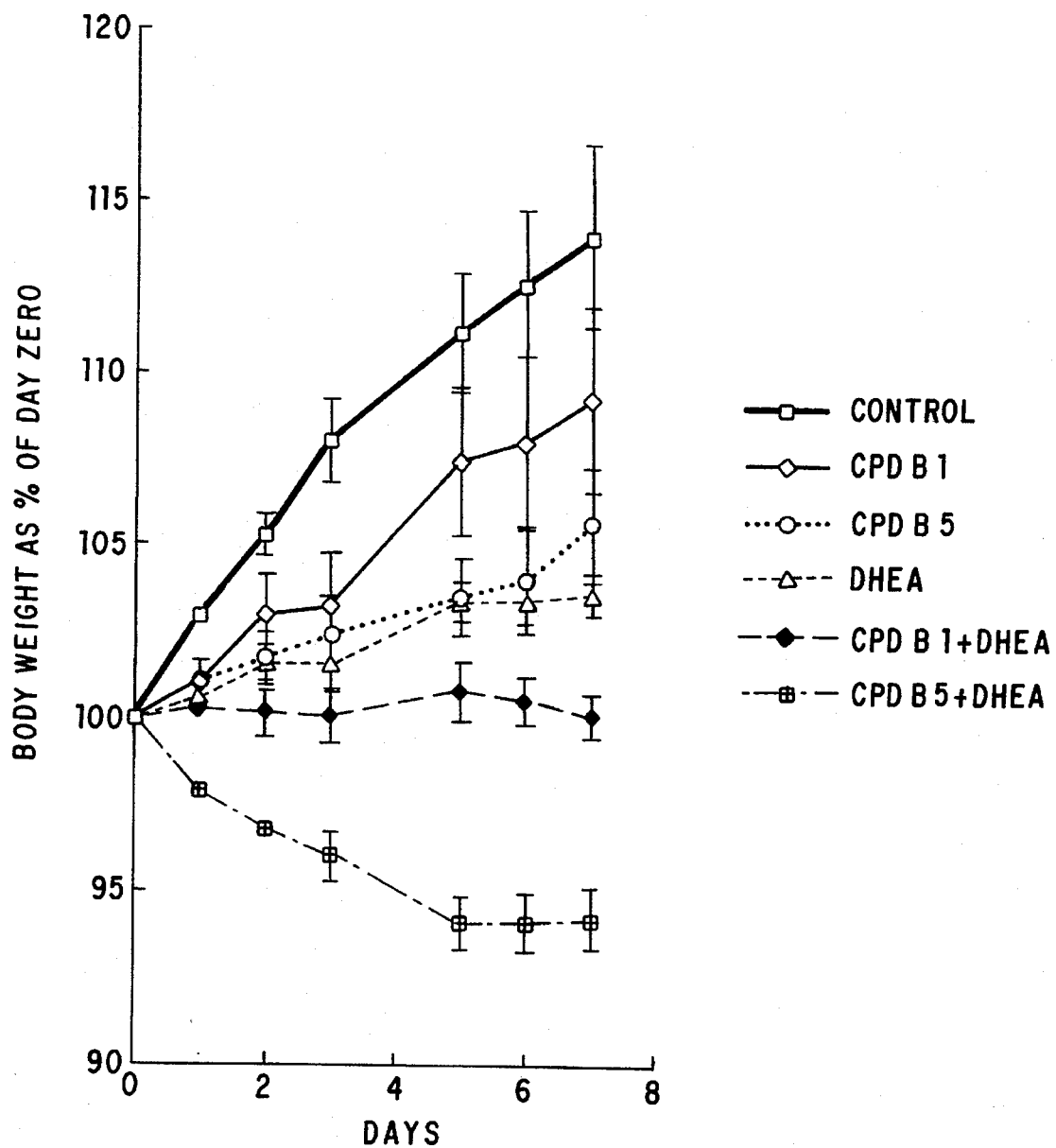
Figure 10A:
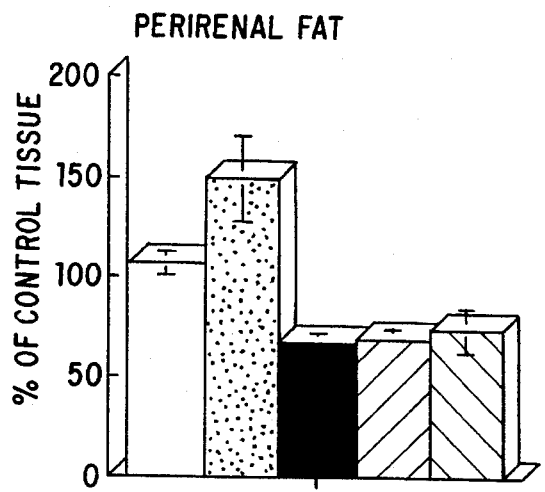
FIGS. 10A, 10B, 10C, 10D: The effect of corticosterone and DHEA individually and in combination on tissue weight of lean Zucker rats is shown. Six groups of animals were established as in FIG. 9. Four tissues were removed from the animals: perirenal fat (A), epididymal fat (B), retroperitoneal fat (C), and soleus muscle (D). Each was weighed. Values are expressed as a percentage of the weight of the control tissue.
Figure 10B:
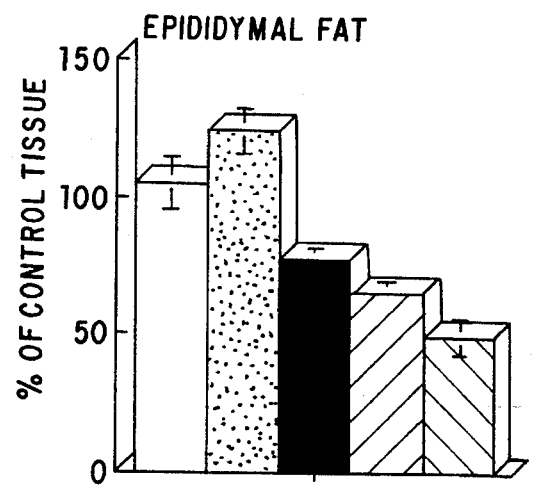
Figure 10C:
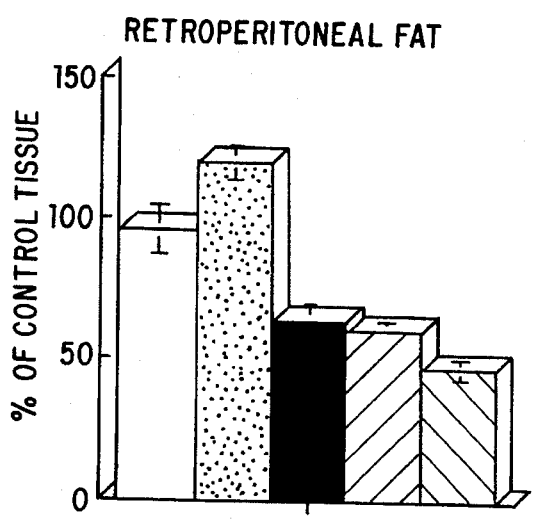
Figure 10D:
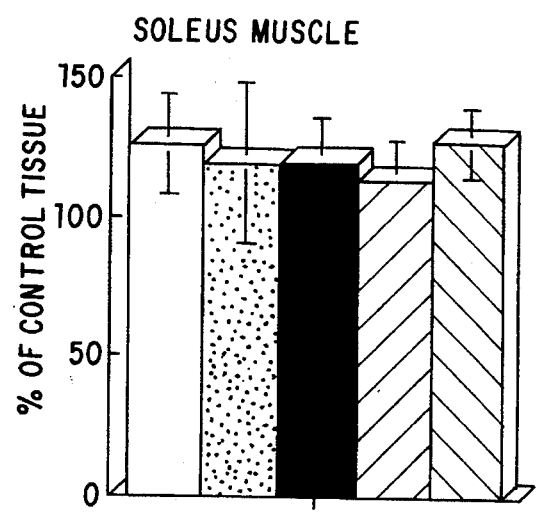

A first group of five animals was treated with 7.5 mg/kg/day phentermine HCl, and a second group of five animals was treated with 7.5 mg/kg/day phentermine HCl and 100 mg/kg/day DHEA for three days. A third group received 100 mg/kg/day DHEA, and a fourth control group of five animals received only vehicle. FIG. 7A shows the daily fat intake, and FIG. 7B shows body weight gain over the trial.

The control group showed the greatest fat intake and increase in body weight, followed by the group administered DHEA alone, and the group administered phentermine HCl alone. The group receiving the combination of phentermine HCl and DHEA evidenced the most significant decrease in fat intake and body weight.

EXAMPLE 8

The effect of diethylpropion HCl and DHEA individually and in combination on fat intake, carbohydrate intake, and body weight of lean Zucker rats was determined.

A first group of five animals was treated with 10 mg/kg/day diethylpropion HCl, and a second group of five animals was treated with 10 mg/kg/day diethylpropion HCl and 75 mg/kg/day DHEA for three days. A third group received 75 mg/kg/day DHEA, and a fourth control group of five animals received only vehicle. FIG. 9A shows the fat intake, FIG. 9B shows the carbohydrate intake, and FIG. 9C shows body weight gain over the trial.

The group administered the combination of drugs showed the greatest decrease in fat intake. The carbohydrate intake and body weight results for the various combinations were inconclusive.

EXAMPLE 9

The effect of corticosterone (Compound B) and DHEA individually and in combination on body weight and tissue weight of lean Zucker rats was determined.

Six groups of animals were established: the first (control) group; a second group receiving an injection of 1 mg/kg/day corticosterone in sesame oil ("Cpd B 1"); a third group receiving an injection of 5 mg/kg/day corticosterone in sesame oil ("Cpd B 5"); a fourth group receiving a diet supplemented with 0.3% DHEA ("DHEA"); a fifth group receiving 1 mg/kg/day corticosterone in sesame oil and a diet supplemented with 0.3% DHEA ("Cpd B 1+DHEA"); and a sixth group receiving an injection of 5 mg/kg/day corticosterone in sesame oil and a diet supplemented with 0.3% DHEA ("Cpd B 5+DHEA").

The animals were fed a "macronutrient selection" diet. The control animals gained the most weight. Animals receiving the lower dose of corticosterone gained almost the same amount as the control animals. Animals receiving the larger dose of corticosterone and animals receiving the DHEA-supplemented diet gained weight, although not as rapidly as the control group and the group receiving the lower dose of corticosterone.

Surprisingly, neither of the groups receiving the combination of DHEA and corticosterone gained weight. In fact, the group receiving the larger dose of corticosterone along with DHEA showed a profound weight loss: the weight of the animals fell to 94% of the original weight.

On the last day of the experiment, all animals were sacrificed and tissues were removed. The effect of the therapies on epididymal, perirenal, and retroperitoneal fat pads was measured. FIG. 10. The weights of the tissues were expressed as percentages of the weights of the control tissues. In each case, treatment with the higher dose of corticosterone caused the greatest weight gain.

In contrast to these results, treatment with corticosterone and DHEA produced a decrease in tissue weight, and at the highest dose of corticosterone, the values obtained are statistically different from both of the corticosterone-alone treated animals.

The effect of these therapies on the soleus muscle is shown in FIG. 10. The weights of the muscle were not affected by DHEA. This indicates that at least some of the weight loss caused by the combined treatment was caused by a preferential loss of fat.

EXAMPLE 10

Metabolites of DHEA, such as Δ4-androstenedione, may substitute for DHEA in the process of the invention. In the present example, the effect of Δ4-androstenedione, on feeding inhibition in lean and obese Zucker rats was determined.

Two groups of five lean animals and two groups of five obese animals were fed control chow for seven days, during which basal caloric intake was measured. A seven day feeding of various concentrations of Δ4-androstenedione determined that concentrations of 0.6 and 0.3% Δ4-androstenedione significantly reduced intake. A final seven day feeding of control chow resulted in an "overshoot" of intake above pre-treatment levels.

After Δ4-androstenedione administration, neurotransmitter content of key hypothalamic feeding centers was measured, including lateral (LH), ventromedial (VMH), and paraventricular (PVN) hypothalamus. After 1 day and seven days of Δ4-androstenedione, the obese Zucker rats exhibited an increased metabolism of 5-HT in LH and PVN, respectively. In addition, dopamine conversion to norepinephrine was increased in VMH.

Serum insulin and Δ4-androstenedione were measured in control and experimental lean and obese Zucker rats. Oral Δ4-androstenedione yielded increased serum Δ4-androstenedione levels compared to their respective controls, indicating that the steroid was in the circulation of the animal. After 1 day of Δ4-androstenedione, insulin levels dropped in the obese Zucker rat, but not in the lean Zucker rat, even though consumption of chow decreased markedly in both phenotypes 24 hours before the animals were sacrificed.

The obese Zucker rat showed a trend toward decreased basal Δ4-androstenedione serum levels compared to the lean Zucker rat. These data suggest that DHEA conversion to Δ4-androstenedione is different in lean and obese rats.

The experimental results show a consistent decrease in the amount of food an obese or lean animal consumes having a particularly striking effect on dietary fat consumption with administration of DHEA and at least one anorectic agent. Most in contrast to treatments currently used to treat obesity and related disorders, the results demonstrate that tolerance to the composition of the invention does not develope over a 28 day period. Given the known activities of DHEA, and the anorectic agents fenfluramine HCl, phentermine HCl, phendimetrazine tartrate, mazindol, diethylpropion HCl, and fluoxetine HCl administered individually, the effect of the combination of the drugs is striking. It is significant that the experimental results were generated not only in the obese animal, which may be a model for some pathologic states of human obesity, but also in the lean animal, the food intake of which is probably a better reflection of normal physiology.

In summary, the combined use of DHEA and an anorectic agent can be a clinically effective treatment for human or animal obesity and related disorders. Currently, there is no other combination that promises to be as effective as the newly discovered combination.

Having now fully described the invention, it will be apparent to one of ordinary skill in the art that many changes and modifications can be made thereto without departing from the spirit or scope of the invention as set forth herein. The appended claims are not intended to be limiting.

We claim:

1. A method for treating obesity in an animal comprising administering a therapeutically effective amount of a composition comprising dehydroepiandrosterone (DHEA) or a derivative thereof and at least one anorectic agent selected from the group consisting of fenfluramine hydrochloride (HCl), phentermine HCl, phendimetrazine tartrate, mazindol, diethylpropion HCl, and fluoxetine HCl, and further comprising the administration of a glucocorticoid.

2. A method for treating obesity in an animal as claimed in claim 1 wherein the derivative of dehydroepiandrosterone (DHEA) is selected from the group consisting of 16-substituted androstanes, 16-substituted androstenes, 17-hydroxysteriods, α-HET, β-HET, and Δ4-androstenedione.

3. A method for treating obesity in an animal as claimed in claim 1 wherein the derivative of dehydroepiandrosterone (DHEA) is Δ4-androstenedione.

4. The method according to claim 1, wherein the glucocorticoid is corticosterone.

5. The method according to claim 4, wherein the corticosterone is administered from about 1 mg/kg/day up to about 50 mg/kg/day.

6. The method according to claim 5, wherein the corticosterone is administered from about 5 mg/kg/day up to about 25 mg/kg/day.

7. A method for treating hyperphagia in an animal comprising administering a therapeutically effective amount of a composition comprising dehydroepiandrosterone (DHEA) or a derivative thereof and at least one anorectic agent selected from the group consisting of fenfluramine hydrochloride (HCl), phentermine HCl, phendimetrazine tartrate, mazindol, diethylpropion HCl, and fluoxetine HCl.

8. A method for treating hyperphagia in an animal as claimed in claim 7 wherein the derivative of dehydroepiandrosterone (DHEA) is selected from the group consisting of 16-substituted androstanes, 16-substituted androstenes, 17-hydroxy-steriods, α-HET, β-HET, and Δ4-androstenedione.

9. A method for treating hyperphagia in an animal as claimed in claim 7 wherein the derivative of dehydroepiandrosterone (DHEA) is Δ4-androstenedione.

10. The method according to claim 7, wherein the composition is administered either orally or parenterally.

11. The method according to claim 10, wherein DHEA or a derivative thereof, the anorectic agent, or both are administered by a method selected from the group consisting of a food supplement, a transdermal patch, a rectal suppository, and by injection.

12. The method according to claim 7, wherein the animal is a human.

13. The method according to claim 7, further comprising the administration of a glucocorticoid.

14. The method according to claim 13, wherein the glucocorticoid is corticosterone.

15. The method according to claim 14, wherein the corticosterone is administered from about 1 mg/kg/day up to about 50 mg/kg/day.

16. The method according to claim 15, wherein the corticosterone is administered from about 5 mg/kg/day up to about 25 mg/kg/day.

17. The method according to claim 7, wherein the composition further comprises a pharmaceutically acceptable carrier.

18. A pharmaceutical composition for treating obesity or a related disorder in an animal comprising dehydroepiandrosterone (DHEA) or a derivative thereof and at least one anorectic agent selected from the group consisting of fenfluramine hydrochloride (HCl), phentermine HCl, phendimerazine tartrate, mazindol, diethylpropion HCl, and fluoxetine HCl, and further comprising the presence of a glucocorticoid.

19. The pharmaceutical composition according to claim 18, wherein the glucocorticoid is corticosterone.

20. The pharmaceutical composition according to claim 19, wherein the corticosterone is present in an amount from about 1 mg/kg/day up to about 50 mg/kg/day.

21. The pharmaceutical composition according to claim 20, wherein the corticosterone is present in an amount from about 5 mg/kg/day up to about 25 mg/kg/day.

22. A pharmaceutical composition for treating obesity as claimed in claim 18 wherein the derivative of dehydroepiandrosterone (DHEA) is selected from the group consisting of 16-substituted androstanes, 16-substituted androstenes, 17-hydroxy-steriods, α-HET, β-HET, and Δ4-androstenedione.

23. A pharmaceutical composition for treating obesity as claimed in claim 18 wherein the derivative of dehydroepiandrosterone (DHEA) is Δ4-androstenedione.

* * * * *